US008598396B2

(12) United States Patent
Beadle et al.

(10) Patent No.: US 8,598,396 B2
(45) Date of Patent: Dec. 3, 2013

(54) OLIGOMERISATION OF OLEFINS

(75) Inventors: Stephen Wayne Beadle, Prairieville, LA (US); John Stephen Godsmark, Grez Doiceau (BE); Robert L. Wolf, Baton Rouge, LA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 908 days.

(21) Appl. No.: 11/912,762

(22) PCT Filed: Jun. 9, 2006

(86) PCT No.: PCT/EP2006/005687
§ 371 (c)(1),
(2), (4) Date: May 12, 2008

(87) PCT Pub. No.: WO2006/133908
PCT Pub. Date: Dec. 21, 2006

(65) Prior Publication Data
US 2009/0221862 A1 Sep. 3, 2009

Related U.S. Application Data

(60) Provisional application No. 60/689,908, filed on Jun. 13, 2005.

(51) Int. Cl.
C07C 2/18 (2006.01)
(52) U.S. Cl.
USPC ........... 585/501; 585/301; 585/302; 585/520; 585/527; 585/529
(58) Field of Classification Search
USPC .......... 585/529, 520, 527, 301, 326, 302, 501
See application file for complete search history.

(56) References Cited

U.S. PATENT DOCUMENTS

| | | | | | |
|---|---|---|---|---|---|
| 2,694,686 | A | * | 11/1954 | Reeves et al. | 502/214 |
| 2,721,889 | A | * | 10/1955 | Murphree et al. | 585/529 |
| 4,153,638 | A | * | 5/1979 | Bercik et al. | 585/526 |
| 4,334,118 | A | | 6/1982 | Manning | |
| 4,440,509 | A | * | 4/1984 | Agarwal | 374/166 |
| 4,675,463 | A | * | 6/1987 | Glivicky et al. | 585/514 |
| 4,709,111 | A | * | 11/1987 | Ward | 585/503 |

(Continued)

FOREIGN PATENT DOCUMENTS

WO  WO 2005/058777  6/2005

OTHER PUBLICATIONS

Perry, et al., "Process Control" in Perry's Chemical Engineer's Handbook, R. H. Perry and D. W. Green, ed., McGraw-Hill, 7th ed., 1997.*
Perry, et al. "Process Control" in Perry's Chemical Engineer's Handbook, R. H. Perry and D. W. Green, ed., McGraw-Hill, 7th ed., 1997.*
Cavani et al., "Effect of water in the performance of the "solid phosphoric acid" catalyst for alkylation of benzene to cumene and for oligomerization of propene," Applied Catalysis A: General, 97, pp. 177-1196 (1993).

(Continued)

*Primary Examiner* — In Suk Bullock
*Assistant Examiner* — Bradley Etherton
(74) *Attorney, Agent, or Firm* — Leandro Arechederra, III

(57) ABSTRACT

Olefin feeds with high olefin content and/or containing a substance that generates water when contacting the catalyst, are oligomerised over solid phosphoric acid catalyst in tubular reactors by introducing the olefin feed into the reactor and maintaining the reacting mixture under conditions whereby the peak temperature is controlled to be below 265° C. and preferably a single liquid or dense phase is maintained and the average temperature throughout the reactor is maintained in the range 190° C. to 260° C.

23 Claims, 3 Drawing Sheets

(56) References Cited

U.S. PATENT DOCUMENTS

| | | | |
|---|---|---|---|
| 5,744,679 A | 4/1998 | Marinangeli et al. | |
| 6,111,159 A * | 8/2000 | Huff et al. | 585/529 |
| 6,550,963 B2 * | 4/2003 | Daily et al. | 374/179 |
| 6,884,914 B2 | 4/2005 | Mathys et al. | |

OTHER PUBLICATIONS

Chitnis et al., "ExxonMobil Olefins to Gasoline: EMOGAS Technology for Catpoly Units," NPRA Annual Meeting, Mar. 13, 2005, pp. 1-18.

* cited by examiner

OLIGOMERISATION OF OLEFINS

CROSS-REFERENCE TO RELATED APPLICATIONS

This application is a national stage filing of International Patent Cooperation Treaty Application No. PCT/EP2006/005687 filed Jun. 9, 2006, which claims priority from U.S. Provisional Application 60/689,908 filed Jun. 13, 2005, the disclosure of which is fully incorporated herein by reference.

FIELD OF THE INVENTION

The present invention relates to improvements in or relating to the oligomerisation of olefins.

BACKGROUND

The condensation reaction of an olefin or a mixture of olefins over an acid catalyst to form higher molecular weight products is a widely used commercial process. This type of condensation reaction is referred to herein as an oligomerisation reaction, and the products are low molecular weight oligomers which are formed by the condensation of up to 12, typically 2, 3 or 4, but up to 5, 6, 7, or even 8 olefin molecules with each other. As used herein, the term 'oligomerisation' is used to refer to a process for the formation of oligomers and/or polymers. Low molecular weight olefins (such as propene, 2-methylpropene, 1-butene and 2-butenes, pentenes and hexenes) can be converted by oligomerisation over a solid phosphoric acid catalyst, to a product which is comprised of oligomers and which is of value as a high-octane gasoline blending stock and as a starting material for the production of chemical intermediates and end-products. Such chemical intermediates and end-products include alcohols, acids, detergents and esters such as plasticiser esters and synthetic lubricants. Industrial oligomerisation reactions are generally performed in a plurality of tubular or chamber reactors. Sulfated zirconia, liquid phosphoric acid and sulfuric acid are also known catalysts for oligomerisation.

Industrial hydrocarbon conversion processes employing acidic catalysts such as those mentioned above typically run for several weeks before a catalyst change is required or a decommissioning of the reactor is needed. In industrial processes the feeds for the reactions are generally obtained from refining activities such as a stream derived from catalytic or steam cracking, which may have been subjected to fractionation. The nature of such refining activities is such that there will be variations in the composition of the feed. In addition it may be desired to change the nature of the feed during a reactor run. The catalyst activity and the reaction conditions vary according to the composition of the feed. Furthermore, the reactions are exothermic and the size of the exotherm also depends upon the nature and amount of olefin present in the feed. Isobutylene and propylene are particularly reactive over solid phosphoric acid catalysts, generating a large amount of heat per unit of mass reacting.

Olefin oligomerization using solid phosphoric acid catalyst may be performed using chamber type reactors, comprising a plurality of catalyst beds sequentially located within one reactor shell and each bed acting as an adiabatic reactor. Due to the reaction heat, the reacting mixture heats up as it passes through a catalyst bed. In between two catalyst beds, a colder diluent stream may be injected to bring the temperature down again before the mixture of the reacting fluid and the diluent enters the following bed. The injection of the colder diluent stream into the reactor is an important element. It is typically preferred to have several spray nozzles at each point of injection, distributed over the reactor cross section such that a maximum of the cross sectional area is covered, and with the spray nozzles preferably but not essentially pointed in the direction against the flow of the process fluid in the reactor. One option is to arrange 4 quench nozzles, approximately 90° apart such as in a cross configuration, each of the nozzles having a full cone spray pattern with a 164° spray angle. An alternative, preferable for a reactor with a smaller diameter, is a simple quench nozzle in the middle, having a hollow cone spray pattern and a 140° spray angle. The hollow cone nozzles with a wide angle are found to cover a wider area, and are therefore preferred. Below and downstream of this quench nozzle arrangement, especially suitable for reactors with a larger diameter and in particular at those locations where 2-phase flow may occur such as in the bottom section of a chamber reactor, a distributor tray may be added, equipped with slotted chimneys and extra tubes depending on the vapor load. All these reactor internals are preferably such that they may be disassembled and removed to provide access to the catalyst beds for removing and replacing the catalyst, after which they may be introduced and assembled again. The top of the catalyst bed may then be further protected against liquid impingement by a layer of inert material, e.g. ceramic balls. This setup provides a better mixing in a minimum volume, thereby reducing the risk for radial temperature and concentration differences and for hot spots in the downstream catalyst bed.

The present invention is concerned with oligomerisation processes that employ a solid phosphoric acid "SPA" oligomerisation catalyst in a tubular reactor.

Tubular oligomerisation reactors employing SPA catalysts typically comprise one or more bundles of tubes, also termed "reactor tubes", mounted, preferably vertically, within a shell, and may be similar to a vertical shell-and-tube heat exchanger. The reactor tubes are packed with the SPA catalyst typically in the form of pellets and the olefin reactant is passed through the tubes in which it is oligomerised, typically from top to bottom. The length of the tube in industrial practice is generally from 2 to 15 meters, preferably from 7 to 12 meters. The diameter of the tube, the thickness of the walls of the tubes and the materials from which the tubes are made are important since oligomerisation reactions are exothermic and it is important to dissipate the heat generated by the oligomerisation reaction. Accordingly relatively small diameter, such as from 3 to 10 cm tubes, are preferred, more preferably 4 to 6 cm diameter tubes. They are preferably of high strength material and are thin walled and of a material with a high thermal conductivity. The high strength is required to withstand the high pressures that are generally used in the oligomerisation of olefins in a tubular reactor employing a SPA catalyst. Duplex stainless steel is a preferred material for manufacture of the tubes.

Any convenient number of tubes may be employed in a reactor shell. Typically, operators use from 10 to 500 tubes per shell, preferably arrayed in parallel. Preferred reactors contain about 77 tubes or 180 tubes per shell, although any number may be employed to suit the needs of the operator, eg 360 or 420. The tubes are preferably mounted within the shell and a temperature control fluid is provided around the outside of the tubes but within the shell to dissipate heat generated by the exothermic reaction that, in use, takes place within the reactor tubes. One reactor may comprise multiple bundles of tubes, for example up to 7 or 8, or even 9 bundles, and preferably, in use, the temperature of the fluid within the tubes in all the bundles in the same reactor is controlled by means of the same temperature control fluid system.

Reference in this specification to removal of heat from the (reactor) tubes or temperature control of the (reactor) tubes is, in context, intended to mean removal of heat from the materials contained within the tubes where reaction takes place (generally comprising, in use, unreacted feed, reaction products and catalyst) and control of the temperature of those materials contained within the tubes. It will be appreciated that the heat generation on the catalyst and heat removal from the tube wall may cause a radial temperature gradient through the cross-section of the tube, such that the center of the tube may become significantly hotter than the wall of the tube. One convenient way to remove the heat from the tubes and carry out the temperature control is to generate steam within the reactor on the shell side around the exterior of the tubes. This provides a good heat transfer coefficient on the shell side. If the present invention is performed in a chemical plant or a refinery the steam generated by the oligomerisation process may be readily integrated into the steam system typically present at such sites. The reaction heat from oligomerisation may then be put to use in another part of the oligomerisation process, or with another process in the plant or the refinery, where heat input is required.

On an industrial scale it is desirable that these tubular reactors can run continuously for as long as possible and that the conversion and selectivity of the reaction is maintained over such extended production runs.

U.S. Pat. No. 6,884,914 relates to the oligomerisation of olefins and provides an olefin feed stream which can be oligomerised at high efficiency. The olefin feed stream may be obtained from oxygenates by treatment with mole sieves. However, refining feeds may also be used, though these are preferably used in admixture with the olefin feed obtained from the oxygenates. The feed preferably contains about 55 wt % olefin and more preferably 60 wt % olefins. U.S. Pat. No. 6,884,914 discusses various different catalysts that can be employed including solid phosphoric acid, although zeolite catalysts are preferred. Here the oligomerisation reaction is performed at a temperature from 170° C. to about 300° C., preferably about 170° C. to 260° C., most preferably about 180° C. to about 260° C. Operating pressure is said to be not critical although the process is carried out at about 5 MPa to 10 MPa. In the oligomerisations exemplified in U.S. Pat. No. 6,884,914, a feed containing 64 wt % butenes is oligomerised using a ZSM-22 zeolite catalyst.

U.S. Pat. No. 6,884,914 is not, however, concerned with optimising oligomerisation of olefins in a tubular reactor employing SPA catalyst. Tubular reactors are the most efficient for oligomerisation reactions over SPA catalyst because the reactions are highly exothermic and require precise temperature control.

As already indicated, the oligomerisation of olefins over a SPA catalyst is a highly exothermic reaction, particularly the oligomerisation of propylene and/or isobutylene. The high temperatures generated can lead to carbonaceous deposits on the catalyst caused by a build up of condensed, heavy hydrocarbons similar to asphalt. Such deposits are commonly termed "coke", and lead to deactivation of the SPA catalyst. In general, the higher the concentration of olefin in the feed, the higher will be the rate of heat release from the catalysed reaction, and hence the higher the temperatures reached. Consequently there will be a higher rate of coke formation. This has placed a limit on the maximum concentration of olefin that can be tolerated in the feed.

The composition of the material in the tubular reactor varies as the material flows through, usually down, the reactor tube and begins to react. The olefin will have a lower molecular weight at the beginning (inlet) of the reactor tube, where it is predominantly unreacted light olefins and it will become progressively heavier towards the tube outlet as the light olefins are oligomerised to form higher molecular weight olefins.

Oligomerisation over a fixed bed of SPA catalyst may show a higher exotherm than over a zeolite catalyst such as ZSM-22. Excessive temperatures coke up the SPA catalyst, which makes it swell. Furthermore, coke also collects in the volume between the catalyst particles. Pressure drop over the SPA catalyst bed then increases to the point that the reactor has to be taken out of service. The spent SPA catalyst bed then has to be drilled out and typically be disposed of as solid waste. A high pressure water lance can be used as an alternative to drilling. However, this produces a waste sludge which is even more difficult to dispose of. The reactor tubes then have to be filled with fresh SPA catalyst and the reactor may then be put into oligomerisation service again.

In the operation of a tubular reactor for oligomerisation of olefin feed, with SPA catalyst in the tubes and a temperature control fluid on the shell side, a temperature profile will be observed over the length of a reactor tube. Conventionally, such operation is performed with the tubular reactor arranged such that the feed inlet is at the top and the reaction product outlet is at the bottom. The following description addresses such an arrangement, but it will be understood that the description applies equally to reactors not in top to bottom arrangement. Thus, the temperature profile initially shows a sharp increase at the inlet of the tube, when reaction heat is generated faster than it can be removed by the temperature control fluid around the tube. As the reactants convert further as they move along the tube and their concentration reduces, the reaction rate reduces and the rate of heat generation reduces. At the same time the temperature in the tube increases, and the heat removal rate increases. The temperature profile then typically goes through a maximum, and then shows a decline further along (down) the tube towards the outlet. As the reaction temperature declines along the tube, also heat removal rate reduces, and the temperature profile may then flatten out before the end of the catalyst bed in the tubes is reached.

With fresh catalyst, the temperature increase at the initial part (eg top) of the tube is sharp, and the temperature profile shows a sharp peak. The fresh catalyst at the initial part (top) of the tube performs most of the reaction. Coke will build up where the temperature is at its highest, which will deactivate the catalyst in that part of the tube. Reaction rate will then reduce in that part of the tube due to the catalyst deactivation, and hence the rate of heat generation will also reduce, and hence the slope of the temperature increase in that part of the temperature profile declines. The catalyst further along (down) the tube will then see a higher concentration of unreacted reactants, and the reaction rate—and hence heat generation rate—will increase in that part of the tube. In this way the peak in the temperature profile known as "the peak temperature" will move along (down) the tube. In order to compensate for the reduced overall catalyst activity, cooling rate is typically reduced by increasing the temperature of the temperature control fluid around the tube. The average temperature in the reactor and the temperature at the outlet of the tube or reactor will thereby be increased. In addition, the inlet temperature to the tube may be adapted as well. Typically it may be increased to keep as much of the reaction as possible at as early (high) as possible a location in the catalyst bed inside the tube. The peak in the temperature profile therefore may not only move along (down) the tube as a production run proceeds but it may also become less sharp and less pronounced.

The rate of heat generation increases with higher reactant concentration. The peak in the temperature profile is therefore sharper and more pronounced when the olefin concentration in the feed to the reactor is higher. The rate of heat generation is also higher with more reactive reactants, typically with the lighter olefins such as propylene and butenes such as isobutylene. The peak in the temperature profile is therefore also sharper and more pronounced when a higher portion of the available butenes is isobutylene, or when a higher proportion of the olefins fed to the reactor is propylene. In case dienes or acetylenes are present, these are even more reactive and will increase the rate of heat generation, in particular in the upstream part of the SPA catalyst bed. The total heat of the reaction also depends on the product produced. The greater the degree of oligomerisation of any particular olefin the higher the heat of reaction, because more monomer molecules will have combined to form the product.

The level of di- and polyunsaturates in the feed is typically controlled to below a maximum allowable level. Preferably, the feed composition is limited to containing no more than 100 ppm by weight of acetylene and/or no more than 500 ppm of the C3 polyunsaturates methylacetylene and propadiene or allene, and/or no more than 2500 ppm or more preferably no more than 1000 ppm of butadiene. The reason for these limitations is the high reactivity and the high heat of reaction of the di- and polyunsaturates relative to their molecular weight. Pentadiene has a heat of reaction that is almost the same as propylene. We have also found that cyclopentene generates substantially the same heat of reaction as pentadiene. We have found that if it is necessary to use feeds containing relatively high levels of polyunsaturates, production may be sustained if the olefin concentration in the feed is reduced accordingly. This keeps the carbon deposition low which would otherwise increase due to the heat generated by the reaction of the higher amounts of polyunsaturates present.

The olefin feed to the tubular reactor is generally a mixture of a reactive olefin and an unreactive diluent, which is typically an alkane. This may have the same carbon number as the olefin. However, it is preferred to have unreactive components present that have a higher carbon number than the feed olefin because of their advantageous effect on phase behaviour in the reactor. The rate of heat generated by the oligomerisation reaction depends upon the concentration of the olefin in the feed. The higher the concentration of olefin the more reactive the feed and the greater the heat that is generated. For example in the operation of tubular reactors employing SPA catalysts to oligomerise propylene containing feeds it has been found necessary to limit the amount of olefin in the feed. This is because, despite employing cooling systems such as the steam generation mentioned previously, it has not been possible to perform extended continuous runs with feeds containing more than 50 wt % propylene. Typically it has only been possible to employ feeds containing much less than 50 wt % propylene, some processes operating at 40 wt % propylene or less.

The feed streams containing the feed olefins such as $C_3$ and $C_4$ olefins are generally refinery steams derived from steam cracking or catalytic cracking, and the composition of the stream will depend upon the raw material from which it is produced and the production technology employed. However, propylene refinery streams typically contain up to 75 wt % propylene with the balance being predominantly propane. Similarly butene refinery streams typically contain up to 70 wt % butenes with the balance being predominantly butanes. The reactivity of the olefins in oligomerisations over SPA catalysts varies according to the nature of the olefin. However it has not been possible to successfully oligomerise $C_3$ to $C_6$ olefins over extended periods of time in tubular reactors employing a SPA catalyst if the concentration of propylene in the feed exceeds 50 wt %, and generally concentrations below 40 wt % have been employed. This has required the expensive addition of diluent to an olefin-containing refinery feed. Typically the diluent may be additional amounts of the alkanes found in the refinery feed and/or it may be provided by recycle of the unreacted material derived from the outlet of the tubular reactor. The need for diluent not only adds to the expense of the operation but it also reduces the volumetric yield of the reaction, with associated economic debits.

In our Patent Application WO 2005/058777, we describe phosphoric acid catalysts and how they may be employed in the oligomerisation of olefins. In particular we describe how the SPA catalyst may be hydrated to improve catalyst performance. These features apply equally to the present invention, and to the porosity profile of the catalyst pellets.

SPA catalysts are typically prepared by combining a phosphoric acid with a support and drying the resulting material. A commonly used catalyst is prepared by mixing kieselguhr with phosphoric acid, extruding the resulting paste, and calcining the extruded material. The activity of a SPA catalyst is related to the amount and the chemical composition of the phosphoric acid which is deposited on the support and to the porosity profile of the catalyst pellets.

Phosphoric acid comprises a family of acids, which exist in equilibrium with each other and differ from each other in their degree of condensation. The catalysts are generally supported on silica and consist of silicon phosphate crystals coated with various phosphoric acids. These acids include ortho-phosphoric acid ($H_3PO_4$), pyro-phosphoric acid ($H_4P_2O_7$), triphosphoric acid ($H_5P_3O_{10}$), and polyphosphoric acids, and the precise composition of a given sample of phosphoric acid will be a function of the $P_2O_5$ and of the water content of the sample. As the water content of the acid decreases the degree of condensation of the acid increases. Each of the various phosphoric acids has a unique acid strength and accordingly the catalytic activity of a given sample of SPA catalyst will depend on the $P_2O_5/H_2O$ ratio of the phosphoric acid which is deposited on the surface of the crystals.

One factor that influences the activity of a SPA catalyst and also its rate of deactivation in an oligomerisation process, is the degree of catalyst hydration. A properly hydrated SPA catalyst can be used to convert over 95% of the olefins in a feedstock to higher molecular weight oligomers. However, if the catalyst contains too little water, it tends to have a very high acidity, which can lead to rapid deactivation as a consequence of coking. Further hydration of the catalyst serves to reduce its acidity and reduces its tendency toward rapid deactivation through coke formation. On the other hand, excessive hydration of a SPA catalyst can cause a change in the crystal structure, leading to lower density and swelling. This change may cause the catalyst to soften and physically agglomerate and, as a consequence, can create high pressure drops in the tubular reactors. Accordingly, there is an optimum level of hydration for a SPA catalyst. In our Patent Application WO 2005/058777, we describe our preferred means of ensuring optimum hydration of SPA catalyst.

During use as an oligomerisation catalyst, a SPA catalyst will develop a degree of hydration which is a function of feedstock composition and reaction conditions. For example the level of hydration is affected by the water content of the feedstock which is being contacted with the catalyst and also by the temperature and pressure at which the catalyst is used. The equilibrium vapour pressure of water over a SPA catalyst in a particular hydration state varies with temperature and it is important to keep the water content of the feedstock at the proper concentration to maintain optimal catalyst hydration and acidity. If a substantially anhydrous hydrocarbon feedstock is introduced with a properly hydrated catalyst, the catalyst will typically lose water during its further use, and will develop a less than optimal degree of hydration. Accordingly when the water content of a feedstock is inadequate to maintain an optimal level of catalyst hydration, it has been conventional to inject additional water into the feedstock. A study of the effect of water on the performance of SPA catalysts as catalysts for the alkylation of benzene with propene and for the oligomerisation of propene is set forth in a review article by Cavani et al, Applied Catalysis A: General, 97, pp. 177-1196 (1993).

As an alternative to incorporating water into a feedstock that is being contacted with a SPA catalyst, it has also been proposed to add a small amount of an alcohol, such as 2-propanol, to the feedstock, to maintain the catalyst at a satisfactory level of hydration. For example, U.S. Pat. No. 4,334,118 discloses that in the polymerisation of $C_3$-$C_{12}$ olefins over a SPA catalyst which has a siliceous support, the catalyst activity can be maintained at a desirable level by including a minor amount of an alkanol in the olefin feedstock. It is stated that the alcohol undergoes dehydration upon contact with the catalyst, and that the resulting water then acts to maintain the catalyst hydration level.

It is also known from, for example, U.S. Pat. Nos. 4,334,118 and 5,744,679 that by using in an alkene oligomerisation process an alkene-containing feedstock with a water content of from 0.05 to 0.25 mol %, and preferably of at least 0.06 mol %, based on the hydrocarbon content of the feedstock, the catalyst becomes deactivated more slowly.

It is also known that when an alkene-containing feedstock has a water content of less than 0.05 mol %, the water content may be increased by a variety of means. For example, the feedstock can be passed through a thermostatic water saturator. Since the amount of water required to saturate the alkene feedstock depends upon the temperature of the feedstock, control of the water content can then be effected by appropriate control of the temperature of the feedstock. The water content of the feedstock is preferably at least 0.06 mol %, based on the hydrocarbon content of the feedstock.

The quantity of water included must be sufficient to accomplish the appropriate hydration of the SPA catalyst in order to provide and sustain the desired catalytic activity. However, as indicated, too much water can cause a swelling of the catalyst leading to deactivation. In some instances an olefin feed to the oligomerisation reactor may contain materials that can decompose on contact with the SPA to form water. For example, a propylene containing stream that is derived from the industrial production of isopropanol may be used as a component of the feed stream for oligomerisation. However, such a stream will generally contain di-isopropyl ether, which, is decomposed by contact with a SPA catalyst to produce propylene and isopropanol, and the isopropanol is decomposed again to propylene and water. The feed may, however, already be saturated with water as a result of the water washing of the feed and typically that water of saturation will be sufficient to optimise the activity of the SPA catalyst. Therefore, the additional water produced by the decomposition of the di-isopropyl ether can result in excess catalyst hydration, and hence earlier catalyst failure.

Therefore, there remains a need to oligomerise olefin feeds containing a higher concentration of olefin using a SPA catalyst over extended production runs in a tubular reactor without undue deactivation or premature failure of the SPA catalyst. There also remains a need to oligomerise feeds containing compounds that generate water on contact with the SPA catalyst over extended production runs without undue deactivation or failure of the catalyst. It will be appreciated that in large scale industrial processes such as are used for the oligomerisation of olefins, small increases in production (such as 1 to 5% increase) have highly significant benefits. In addition, the ability to increase a run length by an apparently small amount also has highly significant benefits.

We have now developed an oligomerisation process that is capable of providing such benefits.

We have found that, regardless of what the overall, average or outlet temperatures of the reactor may be, if the peak temperature is allowed to reach too high a level, the catalyst deactivation rate and the coke build up rate becomes excessive, the catalyst swelling becomes excessive, and the life of the catalyst bed is reduced. We have also found that control of the peak temperature enables water-producing feeds to be processed without the water unduly deactivating the catalyst.

We have found that in order to obtain good catalyst life in an oligomerisation process comprising a tubular reactor containing SPA catalyst, it is important to control the peak temperature at all times and this is more important than to control the overall or average or outlet temperature of the reactor.

SUMMARY OF THE INVENTION

According to the present invention there is provided a process for oligomerising an olefin comprising contacting the olefin with a solid phosphoric acid catalyst in a reactor tube of a tubular reactor having a shell that contains a temperature control fluid for removing heat of reaction from the reactor tube, in which process the olefin feed to the reactor contains at least 42 wt % of olefin and/or contains a substance that generates water when contacted with the catalyst, wherein operating conditions are controlled such that material exiting the reactor tube is at a pressure of at least 55 barg and wherein the shell side temperature control fluid parameters are controlled such that the peak temperature in the reactor tube is no higher than 265° C.

Stated alternatively, the present invention provides a process for the oligomerisation of one or more olefins comprising oligomerisation of the olefin in a tubular reactor employing a solid phosphoric acid catalyst in which the olefin feed to the reactor contains at least 42 wt % of one or more olefins and/or contains material that generates water when contacted with the solid phosphoric acid catalyst, wherein the olefin is fed to the reactor so that the outlet of the tubular reactor is maintained at a pressure of at least 55 barg and wherein the temperature of the shell side in the tubular reactor is maintained with a temperature control fluid whereby the peak temperature is controlled to be no higher than 265° C.

We have found that, provided these conditions are employed, feeds of single olefins and mixtures of olefins can be continuously processed in tubular reactors employing a SPA catalyst over extended runs, for example up to 30 or even 40 days and typically from 15 to 25 days continuous operation, without excessive pressure drop build up. The maximum concentration of olefin in the feed that can be processed will depend upon the nature of the olefin or mixture of olefins that is to be oligomerised. However, we have found that propylene-containing feeds that contain eg up to 65 wt % propylene, more typically up to 60 wt % propylene, even more typically up to 55 wt %, or up to 52% or most typically up to 50 wt % propylene can be employed. Similarly we have found that butene-containing feeds that contain eg up to 70 wt % butene, typically up to 65 wt % butene, most typically up to 60 wt % butene can be processed. Similar amounts can be processed when mixed feeds are employed. The minimum amount of olefin in the feed, according to the invention, is preferably 42 wt %. In the case where the feed contains propylene, the more preferred minimum is 44 wt %, yet more preferably 46 wt % and most preferably 48 wt %. In the case where a butenes feed is employed, the more preferred minimum is 46 wt %, yet more preferably 50 wt %, such as at least 55 wt % and most preferably 60 wt %.

We have also found that if the feed contains species that will generate water on contact with the SPA, such as a propylene feed containing di-isopropyl ether, the water generated will not damage the catalyst even if water is already present in the feed if the temperature is increased to compensate for the additional water providing the peak temperature is maintained below 265° C.

DETAILED DESCRIPTION OF THE INVENTION

We have found that control of the peak temperature is critical for satisfactory performance of the oligomerisation of $C_3$ to $C_6$ olefins over a SPA catalyst in a tubular reactor. The peak temperature may be measured by inserting a multipoint thermocouple in at least one of the reactor tubes. Spider-shaped inserts may be used to keep the thermocouple in the center of the tube. It is preferred that the thermocouple can detect the temperature at various locations along a significant portion of the length of the tube, preferably towards the inlet end of the tube. Desirably, temperature is measured over at least the first 50%, or possibly 75% of the length of the tube from the inlet end, and at a plurality of points. For example it is preferred to make measurements at from 10 to 20 points, such as 15 points, in a tube that is 3 to 10 meters (approx 10 to 33 feet) in length. It is preferred and typically sufficient with SPA catalyst to only monitor temperatures in the initial (top) half, or in the initial (top) 4-5 meters of the 10 meter tube, because due to catalyst swelling and agglomeration, the thermocouple may otherwise be more difficult to remove before drilling out the spent catalyst. The parameters of the temperature control fluid contained within the tubular reactor, for example the temperature, the pressure and/or the flow may then be adjusted in response to the temperature measured by the thermocouples in order to maintain the peak temperature in the tube within the desired range. The peak temperature is preferably maintained below 260° C., more preferably below 250° C., yet more preferably below 240° C. and most preferably below 235° C. Where the reactor consists of a number of parallel tubes, a multitude of those tubes may be provided with a multipoint thermocouple although this is not essential.

Figure 1:
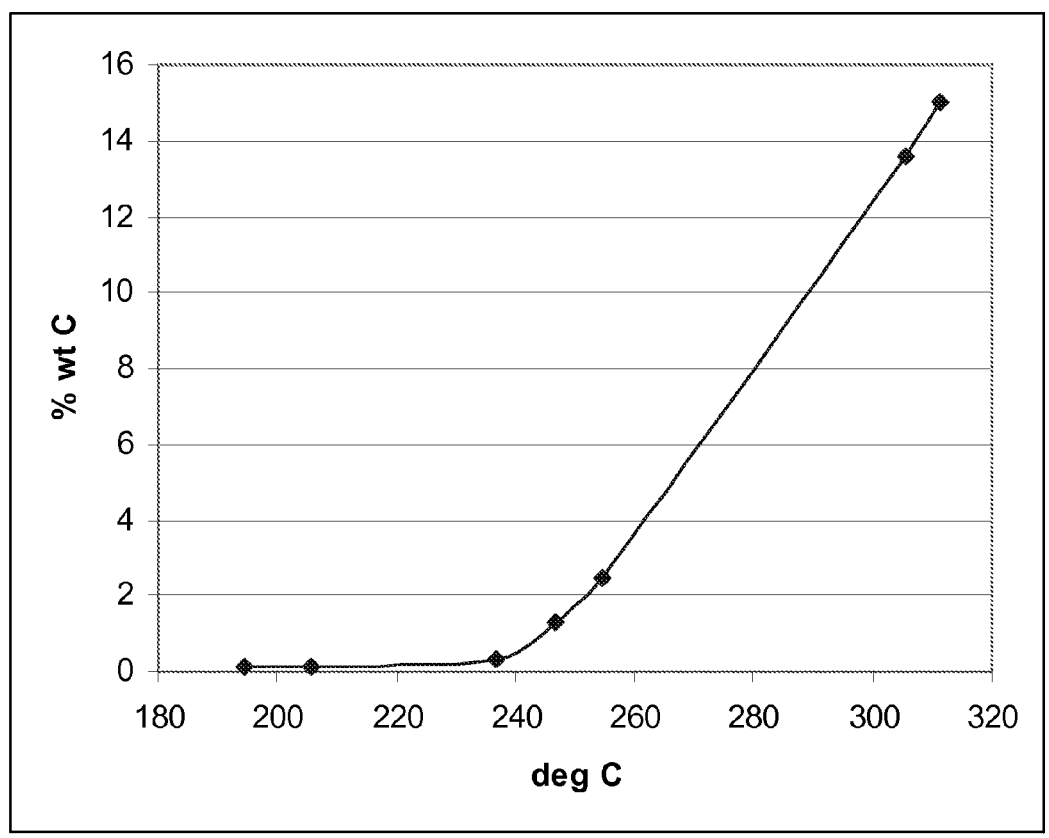
FIG. 1 is a plot of the amount of carbon that was found on spent SPA catalyst as a function of the average peak temperature that was observed over a reactor run in an embodiment of the invention.

The finding that peak temperature control is so critical to avoiding excessive coke build-up and therefore excessive swelling of the catalyst is illustrated in FIG. 1, which shows the amount of carbon that was found on spent SPA catalyst as a function of the average peak temperature that was observed over a reactor run covering 100 hours of operating time and running C3 to C6 olefin feed at an exit pressure of at least 55 barg. The curve shows a low coke build up below 235° C., but a surprising break point slightly above this 235° C. and a rapid increase of the coke build up as the peak temperature was allowed to go up beyond 260° C. or 265° C.

The temperature of the tubular reactors is conveniently controlled by passing a temperature control fluid around the shell side of the reactor tubes. In a preferred embodiment the tubular reactor consists of several tubes mounted vertically and in parallel and they may be mounted as a bundle or bundles of tubes. It is preferred that the olefin feed be introduced at the top of the tubes such that it passes through the tubes in a downward direction. The tubes are preferably contained within a reactor shell and the temperature control fluid preferably flows vertically upwards within the reactor shell in counter current to the direction of the flow of the olefin feed.

Alternative arrangements may comprise co-current upflow or co-current downflow. Co-current flow of the reacting mixture and of the temperature control fluid may offer the advantage, particularly with fresh catalyst, that the temperature control fluid around the tube is colder at the end of the tube where the temperature peak occurs. This provides a better cooling at the location of the peak temperature, and improves the peak temperature control and therefore also the catalyst life.

In one embodiment of the invention the temperature control fluid may be hot oil. However, in a preferred embodiment the temperature control fluid is water, preferably maintained at pressure in the range of 5 to 30 bar gauge, which by boiling results in a temperature in the range of 160 to 235° C. The temperature of the water may be controlled by varying the pressure in the steam drum that separates steam from the boiling water, provides the water for boil up on the shell side of the reactor and collects the shell side outlet stream. In this way the peak temperature, wherever it may occur inside the reactor tube may be controlled to be no more than 265° C. We prefer that the peak temperature be controlled to be no more than 245° C., more preferably no more than 235° C. The lowest reactor temperature, which is typically the inlet temperature, is preferably maintained at or above 140° C., because at temperatures below 140° C. phosphate esters may form in the reactor which then may hydrolyse downstream in the process and liberate phosphoric acid that is corrosive for many construction materials. In preferred operations the lowest temperature in the reactor tube is kept at least at 180° C., more preferably at least at 190° C.

The improvements of the present invention are derived from effective control of the reactor temperature profile and also by employing feed delivery conditions, eg an inlet pressure, that establishes a minimum reactor outlet pressure. It is believed that these pressure conditions maintain the material in the reactor tubes of the tubular reactor in a single phase which may be a liquid phase or a dense phase. A significant vapour phase and a two phase system such as a vapour/liquid phase system should preferably be avoided and particularly is preferably avoided along the entire length of the tube.

There are several ways to establish whether a known stream composition is subject to a 2-phase flow regime under a particular combination of pressure and temperature conditions. Two experimental ways comprise physically preparing a sample of the particular stream composition and introducing this into a high pressure cell. The desired pressure and temperature conditions are then created inside the cell, typically by compressing the cell volume combined with heating and/or cooling. The content of the cell is made homogeneous for a limited amount of time, by intimate mechanical mixing. The mixing is then stopped and the content of the cell is allowed to come to rest. If the cell is equipped with an inspection glass, the visual observation of the presence of an interphase is the first indication of whether the mixture composition separates at these conditions into 2-phases or not. Sampling minute quantities of the cell content from the top and from the bottom of the cell, followed by chemical analysis and comparing the analytical results, provides a second indication. If materials at the top and bottom of the cell are of the same composition, the fluid in the cell is in a single phase. If the composition of materials at the top and bottom are different, two phases are present in the cell, and the cell content is in a 2-phase regime. The compositional information also provides knowledge about the vapor/liquid equilibrium at the cell conditions. By exploring a sufficiently large area in the Pressure-Temperature diagram, the 2-phase (P,T) envelope for the particular mixture may be determined. The critical pressure and critical temperature may then be read from the diagram where the 2-phase envelope reaches the highest pressure. The equilibrium data may also be used to calibrate the coefficients of a chosen thermodynamic equation-of-state for individual mixture components. If sufficient of such thermodynamic data have been determined, the resulting thermodynamic equations may then be used as a third way to determine the state of a particular composition under particular pressure and temperature conditions, by simulation using a computer programme. These simulations are commercially available from a number of engineering programming service providers.

We have found that the present invention may be accomplished with extended runs if the feed material is fed to the reactor under a pressure such that the material exiting from the outlet of the tubular reactor is maintained at a pressure of at least 55 barg and thereby the inlet pressure will also be greater than 55 barg. Preferably the outlet pressure is in the range 60 to 80 barg and more preferably at least 65 or 70 or 75 barg. At the start of a run the pressure drop can be as low as for example 1 bar and we also prefer that the pressure drop across the length of the tubular reactor be no more than 25 bar, more preferably no more than 20 bar, most preferably no more than 15 bar. It is believed that these conditions maintain a substantial portion of the material in the tube in a single phase. The inlet pressure is the outlet pressure plus the pressure drop over the reactor.

According to the invention the lowest pressure for the tubular reactor outlet is 55 barg. As the composition changes throughout the length of the tube, the two phase envelope in the Pressure-Temperature diagram of the material within the reactor tube changes. The critical point of the reacting mixture moves up in temperature and in pressure as the reaction proceeds. The critical point of the mixture marks a limit to the 2-phase envelope of the mixture, so that at pressures above the critical pressure of a fluid, this fluid is not able to separate into a liquid and a vapor phase, and no 2-phase flow is able to occur, regardless of the fluid temperature. It should be understood that the critical point of the reaction mixture, and its 2-phase envelope, is dependent on the composition. It is therefore dependent on the amount and nature of the olefins and paraffins in the reactor feed, and on the conversion and selectivities obtained during the reaction. We have found that running the process under conditions such that the reactor outlet pressure is below 55 barg creates the risk that at some points along the reactor tube, the conditions are inside the 2-phase liquid/vapour envelope. If this happens to a significant degree, it causes the fluid to separate into a vapour and a liquid phase, with the liquid phase containing more of the heavier molecules. As the liquid preferentially stays on the catalyst, this increases coking rate and therefore catalyst deactivation and swelling rate and hence reduces catalyst life and run length. A 2-phase regime also reduces heat transfer from the inside of the reactor tube to its wall, so that the temperature in the middle of the tube becomes higher, again enhancing the coking rate. In order to reduce the risk of having 2-phase flow regime anywhere in the reactor, the outlet pressure is preferably kept above 60-61 barg, more preferably above 65 barg, and most preferably above 68 barg and is ideally maintained at least at 70 barg for as long as possible in the duration of the reactor run length. The pressure let down to 55 barg is typically downstream of the reactor, so typically the reactor outlet pressure starts at 68-69 barg and reduces down to 55 barg during the run. An alternative mode of pressure control is to control the outlet pressure at 55, preferably at 60 or more preferably at 65 barg, and have the reactor inlet pressure increase as the pressure drop over the reactor increases through the run, up to the maximum pressure that the inlet equipment can handle. This could be as high as 82 or 83 barg at the end of the reactor run and is typically no more than 90 barg.

We have also found that the phase behaviour may be further affected by the selection of the diluent that may be added to the reactor feed. We have found that a diluent comprising one or more paraffins having a higher carbon number than the feed olefin is preferred over a diluent with only paraffins of the same or lower carbon number than the olefin feed. During oligomerisation of primarily propylene over solid phosphoric acid catalyst, the presence of normal butane and/or isobutane in the diluent has been found to improve catalyst life.

Deactivation of a SPA catalyst during its use to catalyse the oligomerisation of olefins, is often believed to be a result of the formation of high boiling polymers as by-products. These by-products can remain on the catalyst and undergo further conversion to higher molecular weight polymers, which resemble heavy tars and in some cases even have the appearance of coke-like material. These materials can coat the catalyst particles and plug pores in the catalyst, thereby causing catalyst deactivation. Accordingly, the process of this invention is ideally carried out at a pressure which is sufficient to maintain a liquid or supercritical (dense) phase of hydrocarbon in contact with the catalyst. This liquid or supercritical hydrocarbon phase maintains conditions whereby the high molecular weight polymers or tar are washed off the catalyst, thereby prolonging the catalyst life. The liquid or dense phase also is more effective in removing heat away from the active sites on the catalyst, thereby suppressing the formation of higher molecular weight polymers or tar.

In the practice of the process of this invention employing a SPA catalyst, the olefin-containing feedstock is contacted with the SPA catalyst at a temperature, pressure and period of time which are effective to result in conversion of at least a portion of the compounds in the feed to the desired oligomer products. For example, the olefin to be oligomerised may be an olefin containing from 3 to 9 carbon atoms, preferably from 3 to 6 carbon atoms. The contacting will generally be carried out at a temperature in the range from about 150° to about 250° C. It will be appreciated of course, that the optimum temperature will be a function of the specific reactants employed and their concentration in the feed. For the oligomerisation of propene and/or $C_4$ olefins the reaction temperature will preferably be in the range from about 190° to about 250° C.

The reactor temperature profile may also be controlled by raising the temperature of the feed to the reactor. The temperature may be raised to, for example, between 160° C. and 190° C. prior to introduction into the reactor and this may be accomplished by the provision of any suitable heating means. In a preferred embodiment the feed is heated by use of the heat generated in the reactor, such as in the steam, that has been used to control the temperature in the shell side of the reactor, or by the heat contained in the reactor effluent.

In most industrial processes, such as those described previously, the refinery feed that is to be used in the hydrocarbon conversion reactions will contain impurities such as polar compounds. These impurities would be detrimental to the hydrocarbon conversion reaction and are frequently removed prior to the reaction, by for instance a water wash. In olefin oligomerisation, the feeds are frequently subject to a first alkaline wash to remove acidic polar species, such as thiols or mercaptans, followed by a weakly acidic water wash. The last water wash typically produces a feed stream which is saturated with water at the temperature at which the water wash is performed and, accordingly, can be used to provide the water for hydration of the catalyst as is required in the reaction.

The present invention is illustrated by reference to the attached FIG. 1 as previously discussed; to FIG. 2, which is a schematic diagram of the operation of a process according to the present invention; and to FIG. 3, which is a sectional view of a reactor tube that may be used in the process of the present invention.

Figure 2:
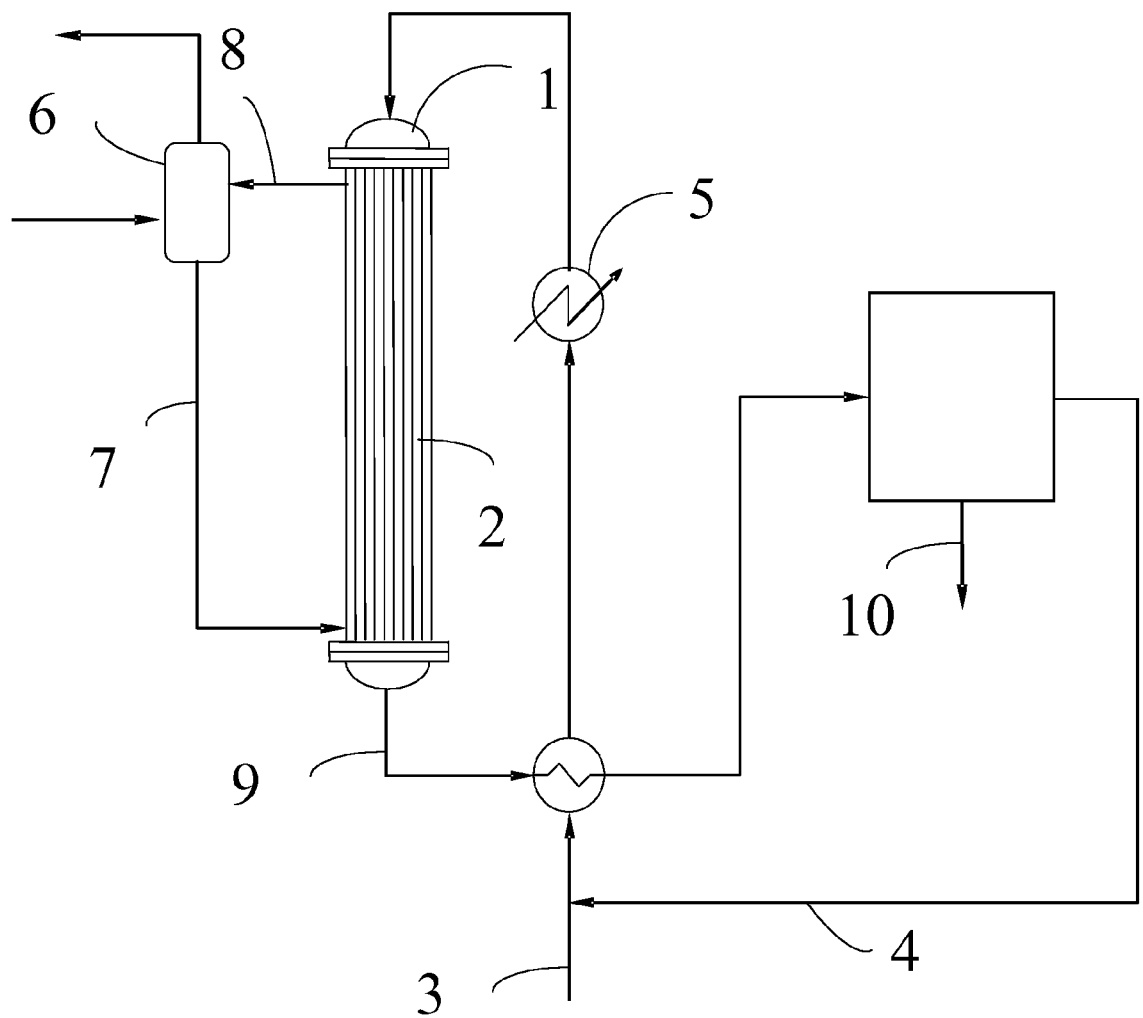
FIG. 2 is a schematic diagram of a tubular reactor designed to perform oligomerization process in an embodiment of the invention.

FIG. 2 shows a reactor shell (1) containing a number of reactor tubes (2). Olefin feed is provided at line 3 and may be diluted to the desired concentration of olefin. In this embodiment the diluent (4) is shown as being recycled unreacted material from the reaction taking place in the reactor tubes. The feed is preheated in heater (5) and passes to the top of the reactor where it passes into the tubes (2) and downwardly over the SPA catalyst that is contained within the tubes.

The temperature within the reactor tubes is controlled by generating steam under pressure within the reactor on the shell side. Water passes from the steam drum (6) to the bottom of the reactor through line (7). It is at least partially converted into steam while cooling the tubes in the reactor, as it passes upwardly through the reactor around the outside of the tubes (2).

The steam and water exiting the reactor may be returned to the steam drum (6) through line (8) for phase separation.

The olefin feed passes down the tubes (2), and is oligomerised. The reaction product exits from the bottom of the reactor through line (9) via which it passes to product separation where the olefin oligomer product is removed at (10).

Figure 3:
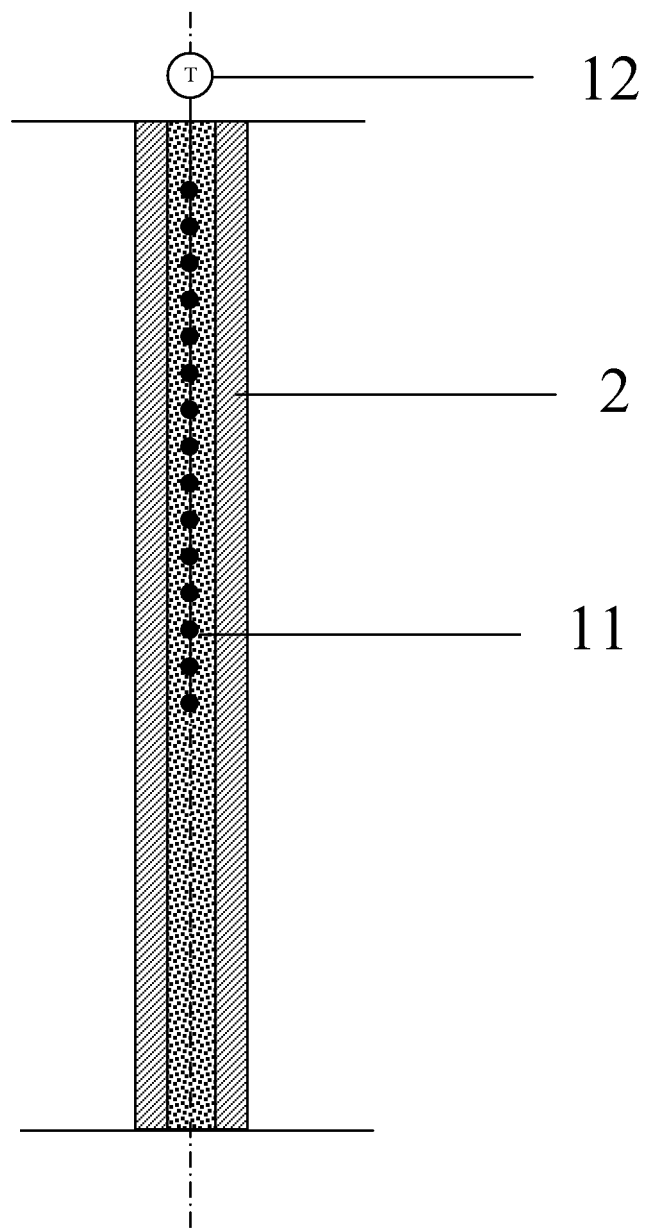
FIG. 3 is a sectional view of a reactor tube that may be used in an embodiment of the invention.

FIG. 3 is a sectional view of a reactor tube (2). The tube (2) is shown filled with SPA catalyst particles (11) and also provided with a 15 point multipoint thermocouple (12) for measurement of the temperature along the initial portion of the tube.

The invention is particularly but not exclusively concerned with processes suitable for the production of $C_5$ to $C_{20}$ olefins boiling in the range of 30° to 310° C., preferably 30° to 300° C., more preferably 30° to 250° C., from propylene and/or butene and/or amylene feedstocks or their mixtures, though ethylene may be present as well. In particular the invention is concerned with the production of the olefins shown in the following table.

| Oligomer Products | Distillation Range (° C.) ASTM D1078 | |
|---|---|---|
| | Initial Boiling Point | Dry Point |
| Pentenes | 30 | |
| Hexenes | 35 | 72 |
| Heptenes | 88 | 97 |
| Octenes | 114 | 126 |
| Nonenes | 135 | 143 |
| Decenes | 155 | 160 |

-continued

| Oligomer Products | Distillation Range (° C.) ASTM D1078 | |
|---|---|---|
| | Initial Boiling Point | Dry Point |
| Undecenes | 167 | 178 |
| Propylene Tetramers Or Dodecenes | 175 | 225 |
| Tridecenes | 204 | 213 |

In certain reactions employing SPA catalyst the catalyst activity and acidity are too high initially, and in these circumstances benefits can be achieved using more water in the olefin feed during the initial period of a reaction run or catalyst life than in later stages once stable reaction conditions and optimal catalyst hydration conditions have been achieved. In such cases it is preferred to employ water during the initial period at a concentration that is from 125 to 300%, more preferably from 150 to 250%, eg about 200% of the concentration that is employed once stable reaction conditions and optimal catalyst hydration conditions have been reached. For example as indicated in our patent application WO 2005/058777, when employing a SPA catalyst, a long life may be achieved if the water content in the feed over the initial phase of the run is in the region of, say, 450 or 500 to 800 or 900 wt ppm. We have found that high activity and conversion is lost if a water content at this level is maintained after the initial period, whereas the high activity and conversion may be sustained if the water content is reduced to within the range of, say, 225 or 250 to 400 or 450 wt ppm once the maximum activity and conversion has been achieved. It is believed that this hydration profile over time contributes to a smoother temperature profile in tubular reactors, and in avoiding temperature excursions in certain parts of the catalyst beds that could cause excessive coking and hence catalyst deactivation. Preferably the initial phase of the run (employing the higher water content) lasts for up to 4 days, during which the peak temperature is preferably controlled to below 235° C. More preferably during the first 3 days the peak temperature is even controlled to below 225° C., this compared to the peak temperature being controlled preferably to below 238° C. for the later part of the run.

In another embodiment, the process of the invention comprises more than one oligomerisation reactor in series, with the product from one reactor being fed to a second downstream reactor. In such a staged reactor setup, the lead reactor may be operated with a high space-velocity, resulting in the temperature profile being spread out, and the peak temperature being lower, hence resulting in a lower coke deposition rate in that lead reactor. The downstream reactor serves to convert the feed olefins that did not react in the lead reactor.

In yet another embodiment, a plurality of oligomerisation reactors is placed in parallel. When the catalysts in the different reactors are not of the same age, this offers the opportunity to adapt the distribution of the total feed over the different reactors to optimize productivity in terms of conversion, temperature control and reactor runlength. This balancing of feed over a set of parallel reactors may be assisted with on-line analyses of the reactor effluents, showing individual reactor conversions, and may be performed automatically by a multi-tiered control algorithm involving time delay calculations to keep the overall process as close as possible to its optimum productivity.

In yet a further embodiment, at the end of the run when the catalyst is unloaded from the reactor, the acidity of the spent catalyst recovered closest to the reactor outlet may be verified analytically. It is preferred that the free acidity of the spent catalyst at the reactor outlet be substantially the same as the free acidity level of fresh catalyst. If the free acidity of the spent catalyst deviates significantly from the preferred level, the hydration target is adjusted in order to better maintain the target free acidity level for the subsequent runs. The free acidity level of the catalyst may be measured by extracting the free acid from the catalyst, preferably with water, followed by titration. It is preferred that the free acidity (i.e. free phosphoric acid content) of the fresh catalyst and the catalyst at the reactor outlet are both within the range 16 to 22%, more preferably in the range 18 to 20% by weight. Any variation in the acidity of the catalyst at the reactor outlet can be an indicator of the need to adjust the water content in the olefin feed stream.

We have also found that, when the hydration is less than optimal on solid phosphoric acid catalyst during a reactor run, more byproduct saturates are made and show up in the oligomer products. The byproduct saturates can be analyzed for example by on-line techniques, such as by Gas Chromatography, or by a Raman analyzer. These techniques are preferably applied on specific narrow-cut oligomer product streams, such as the nonene and/or tetramer product streams from propylene oligomerization, because these streams contain fewer components that may impair the analysis. An increase in the paraffin content in one or more of the products that are analyzed may then provide an additional indication that the amount of water in the feed to the solid phosphoric acid catalyst needs to be increased.

The reactor may be provided with means that enable the reactor to be depressurised to flash off water if the water content in the reactor exceeds the desirable level. This can allow the control of water content under circumstances where an undesirable build up of water would, in other circumstances, require the reactor to be decommissioned. It also allows the operator to correct promptly, before excessive damage is done to the catalyst, for a fresh catalyst that may have been delivered and loaded in overhydrated condition, or when operational upsets have caused the catalyst to become overhydrated. Tubular reactor systems are typically equipped with a vacuum system to evacuate the reactor tubes, and this vacuum can be activated to assist the flashing from the catalyst of water and also hydrocarbons. We have found that this treatment on a SPA catalyst enables recovery of some of the activity lost and also enables reduction of some of the pressure drop that may have built up during the earlier part of the run.

We prefer to apply vacuum to the reactor shortly after it is taken out of service. We have found that this removes residual hydrocarbons, preventing the buildup of even heavier hydrocarbons and permitting easier removal of the catalyst. This may be because hydrocarbons rapidly vaporising in the catalyst pores break up the catalyst pellets and/or agglomerates formed during operation. It has also been found beneficial to include such a flash-off or vacuum treatment in the procedures following an emergency or standby shutdown of the reactor, as it removes a significant portion of still reactive hydrocarbons from the catalyst. It therefore reduces coke build up by preventing condensation reactions on the catalyst. We have found that with this procedure, the catalyst in the reactor typically will maintain or gain activity compared to pre-shutdown when it is subsequently put into service again after the emergency or standby shutdown.

Unreacted olefin is generally recycled to the reactor and here again the water content and impurities content of the olefin recycle feed can be monitored and adjusted to optimise the reaction conditions. Alternatively such recycle is mixed with the fresh feed before the water wash step, and hydration control is effected on the combined stream.

The alkenes that may be oligomerised by the processes of the invention include propene, and linear or branched $C_4$-$C_6$-alkenes, which may be mono-, di- or polyunsaturated. The process is particularly advantageous for the oligomerisation of propene and butenes especially isobutylene and may be used for the oligomerisation of a single alkene, or of mixtures of alkenes of the same or of different carbon numbers. The products made by the oligomerisation are mainly the true oligomers of the starting olefins, such as hexenes, but primarily nonenes and dodecenes, starting from propylene, and octenes starting from butenes. Other carbon number olefin products are made via side reactions involving cracking of oligomer products to shorter chain olefins that are not the same as the starting olefin(s). As such, propylene oligomerisation may yield an amount of octene product.

We have found that coproduction of octene from a predominantly propylene feed may be desirable, and in such case octene production can be promoted by adding pentenes to the propylene feed to the oligomerization reaction. However, we have found that this addition of pentenes in propylene oligomerization may affect the quality of certain products, in particular it may affect the isomer distribution, the specific gravity, the viscosity and the refractive index of the dodecenes or propylene tetramer, and of its derivatives such as isotridecyl alcohol and its adipate and/or phthalate derivative. It is therefore preferred to add not more than about 12% wt of pentenes as a percentage of the total contained olefins in a propylene oligomerisation feed. For consistency of product qualities, it is preferred to have at least 5% wt, more preferably at least 6% wt of pentenes and even more preferably at least 8% wt of pentenes as a percentage of the total contained olefins in a propylene oligomerisation feed.

Oligomerisation of propylene over solid phosphoric acid catalyst may give rise to a small amount of pentene product, due to side-reactions or ethylene in the feed. These pentenes in the reactor effluent may end up in the overhead of a depentenizer tower, optionally together with some more butenes and/or hexenes and even some propylene. We have found that recycling at least part of this depentenizer overhead to the oligomerization reaction may improve overall olefin utilization and, similar to adding pentenes to the feed, may also have a beneficial effect on the phase behaviour in the reactor and on the catalyst life.

The olefin containing feeds for oligomerization may come from a variety of sources, and hence have a wide range of compositions. Traditional sources are steamcracking, catalytic cracking and more recently also methanol-to-olefins processes. The $C_3$ stream from catalytic cracking may, depending on cracking severity, contain for example from 50 to 60% wt of propylene, or higher such as 65% or more, or 70% or above such as 72% wt or 75% wt or even up to 79% wt. The $C_3$ stream from steamcracking may, depending on its sourcing in the steamcracking product cleanup process, contain from 5 to 95 wt % of propylene, for example 92 to 94% wt for chemical-grade propylene, or 25 to 50% propylene for a raffinate byproduct stream from the production of chemical-grade propylene. Less traditional are propane or butane dehydrogenation processes as sources of oligomerisation feeds. Even less known but suitable sources may be described as follows. Residue gas from the production of isopropanol manufacturing may provide a propylene containing stream comprising about 5 to 30% wt propylene, typically 6 to 25% wt, more typically 8 to 10% wt propylene, and further comprising between 0.1% wt to 2.2% wt, typically about 0.7% wt of diisopropylether (DIPE) and between 0.04% wt to 0.6% wt, typically about 0.12% wt isopropanol, the remainder mainly being propane but also including some C6, C9 and C12 hydrocarbons formed in the isopropanol process. This stream contributes to the diluent effect in the oligomerisation process. In addition, the heavies it contains are removed with the oligomer products, so that they do not appear in the final product propane stream. The oxygenates are precursors for water formation in the reactor, and therefore have to be taken into account for the catalyst hydration control.

We have also found that when the concentration of DIPE in the oligomerisation feed increases above what is acceptable for maintaining an optimum catalyst hydration, the negative effect of the excess water on the catalyst may be partially compensated for by increasing the reaction temperature. This helps to keep the achievable catalyst life up, which would deteriorate much more if no compensating action were taken. We have also found that when DIPE concentration increases, there is a noticeable effect on the physical properties of some of the derivatives, in particular those of the dodecene oligomer or propylene tetramer product. When this oligomer product is converted to isotridecyl alcohol through cobalt hydroformylation followed by hydrogenation, and the alcohol is converted into di-tridecyladipate (DTDA) or di-tridecylphthalate (DTDP) esters, we have found that the density of this DTDP is lower, and the viscosities of this DTDA and this DTDP are also lower as compared to when the DIPE concentration is lower or when DIPE is absent in the propylene containing feed to oligomerisation.

Cokers and flexicokers may also provide suitable olefin feed streams. In their C3 cut, these typically contain between 35 and 50% wt propylene, typically around 43% wt. In their C4 cut, one typically finds from 14 to 20% wt butene-1, typically about 17% wt, from 7 to 13% wt isobutylene, typically about 10% wt, from 20 to 30% wt of butene-2, typically about 25% wt, from 30 to 40% wt n-butane, typically about 35% wt, and from 5 to 9% wt isobutane, typically about 7% wt. It may also contain about 3-5% wt butadiene, a level that may be reduced prior to oligomerisation by selective hydrogenation to n-butenes or n-butane. These coker streams may be used as a mixture of different carbon numbers, in which the C3 cut may represent from 40 to 55% wt of the total mixture, typically about 50% wt, the C4 cut may represent from 40 to 50% wt of the mixture, typically 45-46% wt, and the mixture may further contain up to 3% of C5's, of which about half may be pentenes, and it may also contain a minor amount of ethylene, such as 0.5% wt.

We have found that triple branched octenes in an octene oligomer product may affect the properties and/or the performance of a derivative, such as the viscosity or the UV stability of the di-isononyl phthalate as a PVC plasticiser. Isobutylene in an oligomerisation feed may lead to the formation of triple branched octenes. An increase in the concentration of isobutylene in the oligomerisation feed, such as in a mixed light ends feed stream, may increase triple branching in the octene product. The mixed light ends stream may for example be a mixture of C3 olefins and C4 olefins including isobutylene from for example catalytic cracking, or from steamcracking. The effect of the isobutylene presence on the octene triple branchiness may be reduced by adding pentene to the oligomerisation feed. The less branched octenes made from the pentenes and propylene may then dilute the triple branched octene molecules coming from the isobutylene.

Ethylene is less preferred in oligomerisation feeds. It is less reactive because it does not readily form carbenium ions on acidic catalysts. Ethylene may be a precursor in the formation of acetic acid, which may cause corrosion downstream of the oligomerisation reactor, such as in the overheads of the first distillation tower, typically called the stabiliser tower, in which typically the unreacted components are removed from the reactor outlet, and where free water may form. Another effect of ethylene, and of ethane, in the oligomerisation feed, is that a few % of C2 hydrocarbons may have a significant effect on the phase behaviour in the oligomerisation reactor. We have found that it is preferred to have not more than 3% wt, preferably not more than 2% wt of C2 hydrocarbons in an oligomerisation feed that is primarily C3, such as 70% wt propylene, the balance being propane, in order not to create less preferred two-phase behaviour in the oligomerisation reactor, which, as discussed hereinbefore, is a potential cause of more coke formation.

Chlorine compounds, and more importantly chlorides, are typically undesired contaminants in oligomerisation feeds, because they may cause corrosion. We have found that phosphoric acid from SPA catalyst may react with the steel, which typically is carbon steel, of the reactor to form iron phosphate, which may form a protective layer on the equipment metal that reduces corrosion rate. However, chlorine compounds, in particular chloride in the form of HCl, strip away this protective layer, making the metal more vulnerable to corrosive attack by acids, e.g. organic acids such as acetic acid. The combination of a chloride and an organic acid may therefore cause even higher corrosion rates than each of these components by itself.

Supported catalysts which are prepared by combining a phosphoric acid with a solid support are referred to herein as SPA catalyst, and any such catalyst can be used in the practice of this invention. A SPA catalyst is normally prepared by mixing a phosphoric acid, such as ortho-phosphoric acid, pyrophosphoric acid or polyphosphoric acid with a siliceous solid carrier to form a wet paste. This paste can be calcined and then crushed to yield catalyst particles, or the paste can be extruded or pelletised prior to calcining to produce more uniform catalyst particles. The carrier is typically a naturally occurring porous silica-containing material such as kieselguhr, kaolin, or diatomaceous earth. A minor amount of various additives, such as mineral talc, fullers earth and iron compounds, including iron oxide can be added to the carrier to increase its strength and hardness. The combination of the carrier and the additives normally comprises about 15-30 wt % of the catalyst, with the remainder being the phosphoric acid. However the amount of phosphoric acid used in the manufacture of the catalyst can vary from about 8 to 80 wt % of the catalyst. SPA catalyst is available commercially, and such materials are available from UOP under the name SPA-1 and SPA-2, or from Süd-Chemie or SCI as the C-84-series and CA-131. The UOP catalysts are cylindrical extrudates which may have the following properties: (1) a nominal diameter of about 6 mm and length/diameter ratio of respectively about 1.7 and 2.7; (2) an average bulk density in the range of respectively 0.91-0.94 and 0.87-0.91 g/cm$^3$; (3) a free phosphoric acid content, calculated as $P_2O_5$, of 17 to 22 wt %; and (4) a nominal total phosphoric acid content, calculated as $P_2O_5$ of 62.5-64.5 wt %. The C-84 series catalysts are also cylindrical extrudates offered in various grades with a diameter of 6.3 mm and lengths of about 10, 17 or 20 mm, average bulk densities in the range of 0.82-0.95, a free phosphoric acid content of 16-20 wt % and a total acid content of 62.0-63.6 wt %. The preparation and properties of commercial SPA catalyst are set forth in U.S. Pat. Nos. 2,120,702; 3,050,472; 3,050,473 and 3,132,108 and also in British Patent 863539.

The distribution of phosphoric acids in a SPA catalyst can be evaluated experimentally by titration of the 'free $P_2O_5$' content of the catalyst, which consists of the acids that are easily leached from the catalyst when it is immersed in water.

These easily leached acids are phosphoric acids which have a low degree of condensation, such as ortho-phosphoric acid and pyrophosphoric acid. The phosphoric acids which have a higher degree of condensation dissolve very slowly when the catalyst is immersed in water, and accordingly are not measured by titration of the acids in the aqueous extract. Therefore the amount of free $P_2O_5$ can be used as an indication of the distribution of phosphoric acids in a catalyst which has a given total $P_2O_5$ content. The total phosphoric acid content can be determined by titration after all the acids have been extracted using a strong base such as caustic soda.

In a preferred embodiment, referred to as "split loading", the reactor tube is filled with two, or sometimes even three, or possibly even more, different types of catalysts that differ from each other in terms of pellet geometry (typically for extrudates expressed as length over diameter or L/D). With a higher L/D of the catalyst, also the void fraction in the catalyst bed increases. This provides more void space for the process fluid to pass through the catalyst bed, and reduces pressure drop per unit of length. A higher void space also allows for more catalyst swelling before a pressure drop across the reactor tube length is reached that is of a value necessitating catalyst change out. It therefore also affects reactor run length. It is therefore preferred to load catalyst having a higher L/D, such as between 2.5 and 3.0, preferably 2.7, in the initial (top) part of the reactor, where coke build up is the highest and therefore also catalyst swelling, and load catalyst having a lower L/D, such as between 1.5 and 2.0, preferably 1.7, in the downstream (bottom) part of the tube. The latter allows more weight of catalyst to be loaded in the downstream part of the reactor tube, and hence increases total catalyst loading and reactivity. More preferred even is to have three layers of catalysts in the tubes, according to this same principle, and catalyst with an L/D between 3.0 and 4.0, preferably 3.5 may also be employed. It is easier in catalyst manufacturing to use catalyst pellets that have the same diameter. So, for a pellet diameter of for instance about 5 mm, the pellet lengths may be adjusted accordingly to be within the range of 7.9-10.5 mm, 12.5-16.0 mm and 16.0-20.1 mm respectively. When the pellet diameter is e.g. 6.3 mm, the nominal lengths may be around 10, 17 and 20 mm accordingly.

Templates may be used when loading a reactor with catalyst, more particularly when split loading is to be carried out. The template technique comprises putting a prefabricated mask over the top face of the reactor tubes when the catalyst pellets are distributed over the reactor tubes. The mask selectively allows catalyst pellets to fall into a predefined number and pattern of tubes, and not into the other ones. The number of tubes in which the mask allows the pellets to enter is preferentially adjusted to the volume of catalyst that is distributed in one operation, or the amount of catalyst taken for distribution is adjusted to the number of tubes left open by the mask and to the average catalyst height intended to be reached for that particular part of the fixed bed. The pattern may be drawn such that the distribution over the tubes left open is most conveniently done. For a second and subsequent batch of catalyst to be loaded, each time a different template may be used, or one template may be designed that can serve for more than one batch, by turning it through a certain angle along a vertical axis over the tubes of the reactor so that the same pattern now covers a complementary set of tubes compared to the previous template position.

When a reactor tube is loaded with catalyst, a standard pressure drop test may be applied to verify whether the tube is sufficiently filled and no significant pockets of void space have been left open that could cause preferential flow to this tube due to a lower pressure drop compared to the other tubes. This may be done by establishing a fixed flow of a vapor or preferably inert gas through the tube and measuring the pressure drop over the tube under these flow conditions. With the bottom of the reactor open to the atmosphere during loading, the measurement consists of reading a pressure gauge on e.g. a nitrogen inlet line connected to the top of the tube, through which a preset flow of nitrogen is pushed out through the tube. If inadequate packing is detected in certain tubes, the catalyst may be at least partially removed and the tube may be reloaded, so that a more uniform flow distribution over the different tubes of one reactor bundle may be obtained.

SPA catalyst is typically drilled out from the tubes of a tubular reactor after the reactor is decommissioned, because the catalyst pellets will have become swollen and typically agglomerated during use. The drill bit is typically driven by compressed air, and the catalyst fines are sucked up by applying a vacuum on the tube during the drilling operation. The catalyst pellets are broken up by the drilling into finer particles that are readily carried away with the air flow. They are then allowed to settle from the air flow and are collected for disposal. This mode of unloading destroys the physical integrity of the catalyst pellet at the time of removal, and mixes the catalyst particles of the various sections of a catalyst tube, so that only limited information can be collected from spent catalyst analysis. At the time of loading therefore, at certain chosen heights in the reactor tube, baskets of catalysts may be placed that may be recovered as such after the reactor has completed its operating run. They typically are cylindrical baskets, having a top and a bottom closure, all made from perforated metal plate and having an outer diameter that closely fits inside the reactor tube. A means is provided for opening the basket and filling it with catalyst. After service, a tube that contains such a basket is then drilled out until the basket is reached. The basket is then recovered, and the rest of the tube may then be drilled out. Several baskets may be placed in the same tube at different heights. After the baskets have been removed as described, the spent catalyst may be recovered from the baskets and its properties may then be tested. This provides a means for testing a different catalyst than what was in the rest of the tube, and a means for making observations about the condition of a spent catalyst at a certain location in the tube. This may lead to increased understanding about the history of operating conditions throughout a reactor run at a particular position along the reactor tube, and may lead to guidance in terms of reaction conditions preferentially to be used or avoided to optimise tubular reactor operations.

In the practice of the invention, when starting up the process the fixed bed of SPA catalyst within the reactor tube may be initially immersed in a start-up fluid. This typically comprises a less reactive or inert hydrocarbon liquid, such liquid preferably being circulated through the reactor to provide heat to the catalyst bed. The desired conditions of temperature and pressure, are then established in the fixed bed of SPA catalyst. A minimum temperature may also be required before start-up, to minimize or eliminate certain side reactions that could occur with reactive feed on insufficiently heated catalyst. A flow of the feedstock is preferably hydrated, then introduced over the catalyst bed under the conversion conditions that were previously established when the catalyst was immersed in the start-up fluid.

With a tubular reactor however, the use of a circulating start-up fluid is not essential as the heat up of the catalyst bed can be accomplished via the temperature control fluid on the shell side of the reactor. When the desired temperature is reached, normal feed may be introduced into the reactor.

The start-up feed comprises an olefin, optionally a diluent, and preferably the appropriate amount of water. The relative proportions of the materials in this feed depend upon the nature of the olefin and the oligomerisation conditions. The reactions are strongly exothermic and accordingly a diluent such as a paraffinic or a heavy olefinic hydrocarbon is generally used. For example when the feed consists of $C_3$ olefins, we prefer that the feed contain from 40 or 42% to 60%, most preferably 48 to 52% by weight of olefins, with the balance being a paraffinic or a heavy olefinic hydrocarbon diluent, such as a $C_3$-$C_5$ refinery paraffinic stream. Such feeds may be readily available as that which may be obtained from a catalytic cracker. Its olefin content may be reduced if needed by recycling of unreacted paraffins or low olefinic streams found elsewhere or recovered from the reactor effluent. If butene is to be oligomerised we prefer to use a feed containing from 50% to 70% olefins.

The fixed bed of SPA catalyst is brought to the desired conversion conditions of temperature and pressure and the olefinic feed then introduced. As previously stated, the feed preferably contains a minor amount of a hydrating agent which is preferably comprised of at least one material selected from the group consisting of water, ethers and monohydric aliphatic alcohols which contain from 2 to 12 carbon atoms, though methanol could also considered as a hydrating agent. The amount of the hydrating agent present in the feed is controlled to be effective to provide the desired level of catalyst hydration. The desired concentration of hydrating agent in the feed will depend upon the reaction. In the initial phase the concentration will desirably be in the range from about 0.05 to about 0.80 mol % and more preferably from about 0.10 to about 0.50 mol % and most preferably from about 0.25 to about 0.30 mol % based on the feed. Ideally, after the initial start-up the amount of the hydrating agent added will desirably be an amount which is capable of providing an amount of water which is just equal to the amount of water required to maintain a particular hydration or free acid level on the catalyst throughout the catalyst run.

Preferred hydrating agents include water, secondary alcohols and tertiary alcohols. Although the invention is not to be so limited, it is believed that the alcohols decompose upon contact with the SPA catalyst to yield water and decomposition products which include olefins that are produced by the acid catalysed elimination of water from the alcohol. The secondary and tertiary alcohols are usually preferred over primary alcohols because they tend to decompose more readily upon contact with the SPA catalyst. Alcohols which contain from 3 to 5 carbon atoms are desirable hydrating agents and such materials include 2-propanol, 2-butanol, 2-methyl-2-propanol, 2-pentanol, 3-pentanol, 3-methyl-2-butanol and 2-methyl-2-butanol. 2-Propanol is a particularly satisfactory hydrating agent. When an alcohol is used as the hydrating agent or as a component of the hydrating agent, and the hydrocarbon conversion involves the use of one or more olefins as reactants, it may be desirable to use an alcohol which has the same number of carbon atoms as the olefin. The olefin produced by the dehydration of the alcohol can then participate as a reactant in the hydrocarbon conversion process and by-products will be minimised. For example, if 2-propanol is used as a hydrating agent for the oligomerisation of propene over a SPA catalyst, any propene produced by decomposition of the 2-propanol will be oligomerised along with the propene in the feed.

Water is a highly satisfactory hydrating agent. Despite the fact that it is relatively insoluble in typical hydrocarbon feeds under ambient conditions of temperature and pressure, it is conventionally incorporated in sufficient concentrations in a hydrocarbon feed to produce a desired level of catalyst hydration. Monohydric aliphatic alcohols which contain from 2 to 12 carbon atoms are ordinarily quite soluble in typical hydrocarbon feed. Accordingly these alcohols are very convenient for use as hydrating agents. Accordingly, one embodiment of the invention involves the use of a hydrocarbon feed wherein the hydrating agent is comprised of a mixture of water and at least one alcohol which is selected from the group consisting of monohydric aliphatic alcohols which contain from 2 to 12 carbon atoms. Such a feed is conveniently prepared by adding one or more alcohols to the hydrocarbon components of the feed which contain water, and wherein the amount of water is insufficient to provide the desired level of catalyst hydration.

The materials obtained from the process of the present invention will generally be a mixture of desired olefin oligomers, unreacted olefins, diluent (if any is used), water and other impurities. The materials are therefore separated, generally by fractional distillation primarily into the olefin oligomers, the unreacted olefins and, if present, the diluent. The unreacted olefins and diluents may be recycled to the oligomerisation reactor. The olefin oligomers may then be purified as required for use in subsequent reactions. For example the oligomers may contain trace amounts of sulphur which may damage a hydroformylation catalyst. Accordingly, if the olefins are to be used as a feed for hydroformylation, the feed may need to be desulphurised. Similarly the olefin oligomers may contain trace amounts of chlorine which may also be detrimental to hydroformylation catalysts and may need to be removed. If the hydroformylation catalyst is not damaged by sulphur or chlorine, the catalyst in the subsequent hydrogenation step to produce the alcohol derivatives may be damaged by these compounds, and hence sulphur and chlorine are preferably removed, most preferably to very low levels. Furthermore the olefin oligomers themselves are frequently mixtures of oligomers of different carbon number. For example oligomerisation of a mixture of propylene, butene and amylene can result in a mixture of $C_6$ to $C_{13}$ oligomers and this mixture can then be separated by fractional distillation to obtain the oligomer or oligomer mixtures desired for a particular purpose.

In a highly preferred embodiment, the process of this invention can be used in connection with the conversion of a mixture of $C_3$ and $C_4$ olefins to gasoline blending stock by oligomerisation. In such an embodiment, the feed will be comprised of at least about 25% by weight of olefins. A typical olefin-containing feedstock to a polymerisation unit for conversion to oligomers in the gasoline boiling range will comprise a mixture of propane, butane, 2-methylpropane, propene, 1-butene, 2-butene and 2-methylpropene, wherein the olefin concentration is in the range from about 35 to about 60% wt. Ethylene and ethane may also be present, albeit typically in minor amounts. However it will be appreciated that the olefin-containing feedstock can have a variety of other compositions which include but are not limited to, other olefins or olefin mixtures, other diluents and the presence of a minor amount of aromatic compounds. In addition olefin concentrations can be used which are outside this range.

In a further embodiment the present invention is used for the oligomerisation of olefins such as ethylene, propylene, butenes and amylenes to produce $C_6$ to $C_{13}$ olefins which can be used as feeds for hydroformylation reactions for the production of aldehydes and alcohols. The aldehydes may then be oxidised to produce acids or hydrogenated to produce alcohols. The alcohols may then be used in the production of synthetic esters such as plasticiser esters or synthetic lubricants or in the production of surfactants. The olefins may be hydroformylated using low pressure rhodium catalysed hydroformylation technology or high pressure hydroformylation technology which is typically cobalt catalysed, but rhodium is also used. The present invention is particularly useful in the production of feedstocks which are hydroformylated in the manner described in our copending Patent Application WO 2005/058787. Where the aldehydes produced by this method are hydrogenated, this may readily be accomplished by the method described in our copending Patent Application WO 2005/058782.

In the present invention the catalyst is contained in a reactor tube, generally a multiplicity of tubes which are surrounded by a circulating cooling medium. Preferably these tubes will each typically have an internal diameter of from about 5 cm to about 15 cm, although other diameters can also be used. A tubular reactor is frequently preferable to a chamber reactor because it permits a closer control of the reaction temperature and can be easily constructed for high pressure operation. Ordinarily a plurality of reactors will be used. For example an olefin oligomerisation unit employing tubular reactors can have as many as eight or more reactors. The temperature in tubular reactors is typically controlled by steam generation in the shell around the reactor tubes. Multiple tube bundles may have their shell side linked up to the same single steam drum.

Selected streams can also be recycled to the reactor to effect dilution or to modify the product slate. For instance, in a propylene fed reactor, $C_6$, $C_9$ or $C_{12}$ olefin streams, fractionated downstream of the reactors, can be recycled to the reactor to modify the product slate distribution. Byproduct streams of carbon numbers other than the above, such as $C_{7-8}$ or $C_{10-11}$ mixtures, can also be recycled to reduce their production, if possible even recycled to their full extinction. The feed to the reactors may also be diluted with such recycle streams. These recycle streams may be introduced in order to achieve one or more effects, eg to affect phase behaviour in the reactor, to improve catalyst life, to control conversion, to control the selectivity towards particular products, or to assist in control of the exotherm and therefore also the peak temperature.

It has been stated before that SPA catalyst is typically drilled out of the tubes of the tubular reactor. The drill bit typically has a smaller diameter than the internal diameter of the tube. The combination of drill motor and drill bit is conveniently designed so that the tube wall cannot be damaged by the drill bit. The smaller diameter of the drill bit typically causes a thin layer of spent catalyst to stay on the inner side of the tube wall. It is therefore preferred to remove this layer of spent catalyst, e.g. by wire brushing the inner side of the tube, in particular the initial (top) section, before the reactor tube is filled with catalyst again. We have found that this removal enhances heat transfer during the operation of the tubular reactor, as well as allowing more fresh catalyst to be loaded per tube.

It has also been found that upon end of the reactor run, the catalyst located in the bottom of the tube, nearest to the reactor outlet, is still in relatively good and active condition. When conditions permit, we have therefore occasionally only drilled out and removed the upper portion of the catalyst bed from the reactor tubes. As a guidance for determining until what depth of the bed the catalyst has been deactivated, the pressure of the vacuum that is applied at the top of the tube during catalyst drilling for catalyst fine removal may be monitored. Typically the pressure is low during drilling the top of the tube, indicating that still a section below the drill bit is relatively tight for the air to come up from the bottom of the tube, which is open to the atmosphere, through the remaining part of the catalyst bed. As the catalyst tube is drilled further, more of this resistance to flow is removed, and at a certain depth the air may flow more freely through the remainder of the bed, resulting in the vacuum being broken and indicating the catalyst in the remaining portion was not substantially fouled during the preceding run, and is still in a relatively active condition. That part of the bed may be kept in place and fresh catalyst may be loaded on top of it.

A problem that may occur with tubular reactors is that the circulation flow of the shell side temperature control fluid is not sufficiently high. In the case of water and steam, this means that there is a high rate of vaporisation within the reactor on the shell side, such that much of the volume in the upper side of the reactor shell side and in the return line to the steam drum is occupied by steam vapor instead of by boiling water. This may impair the heat transfer in the upper part of the reactor tube or bundle of tubes, which makes the temperature profile inside the tube sharper and more difficult to control below a maximum limit. When colder boiler feed water is introduced in the steam drum below the liquid level, the temperature of the water flowing from the steam drum to the reactor shell side may become subcooled to below its boiling temperature, which also impairs heat transfer at the lower end of the tube bundle because the heat exchange is not immediately in the boiling regime. We have found that this problem may be alleviated by the solution suggested in our copending patent application PCT/US2006/06014.

An alternative way to control the temperature profile along the reactor tube, is to have the shell side temperature control fluid flow in co-current mode with the process fluid which can provide the temperature control fluid at its lowest temperature close to the position where the process fluid is at its highest temperature. This may be achieved by forcing the circulation of the water from the steam drum from top to bottom on the shell side, in the case where the reactor tubes are arrayed vertically with their inlets at the top. This creates a risk of vapor pockets on the shell side, but this may be alleviated by providing vent tubes returning to the steam drum. It may alternatively be accomplished by having the process fluid moving upwards inside the reactor tubes while the temperature control fluid flows from bottom to top, for example by forced flow or simply driven by thermosyphon.

The invention claimed is:

1. A process for oligomerising a feed containing an olefin comprising contacting the olefin with a solid phosphoric acid catalyst in a reactor tube of a tubular reactor having a shell that contains a temperature control fluid for removing heat of reaction from the reactor tube, in which process the olefin feed to the reactor contains at least 50 wt % of olefin and/or contains a substance that generates water when contacted with the catalyst, wherein operating conditions are controlled such that material exiting the reactor tube is at a pressure of at least 55 barg and wherein the shell side temperature control fluid parameters are controlled such that the peak temperature in the reactor tube is no higher than 265° C.; wherein the fresh catalyst and the catalyst at the reactor tube outlet both have a free acidity within the range of 16 to 22% by weight.

2. The process according to claim 1 in which the feed comprises an olefin having from 3 to 6 carbon atoms.

3. The process according to claim 2 in which the feed comprises up to 65 wt % propylene.

4. The process according to claim 3 wherein the feed comprise propylene and from 5 to 12 wt % of the olefins in the feed are pentenes.

5. The process according to claim 4 in which the feed comprises up to 70 wt % butene.

6. The process according to claim 1 wherein the feed comprises not more than 3 wt % $C_2$ hydrocarbons.

7. The process according to claim 1 in which the tubular reactor comprises a plurality of reactor tubes arranged vertically and the olefin feed is introduced at the top of the tubes and passes through the tubes in a downward direction.

8. The process according to claim 1 in which the temperature control fluid flows within the reactor shell counter current to the direction of the flow of the olefin within the reactor tube.

9. The process according to claim 1 in which the material exiting the reactor tube is at a pressure of at least 60 barg.

10. The process according to claim 9 in which the pressure is in the range 60 to 80 barg.

11. The process according to claim 1 in which the feed is contacted with the catalyst at a temperature in excess of 140° C.

12. The process according to claim 1 in which the temperature of the feed is raised to between 160° C. and 190° C. prior to introduction into the reactor tube.

13. The process according to claim 12 in which the feed temperature is raised by means of heat generated in the tubular reactor selected from heat from the shell side temperature control fluid and heat from the reactor tube effluent.

14. The process according to claim 1 in which the solid phosphoric acid catalyst is hydrated.

15. The process according to claim 14 wherein the temperature is in excess of 180° C.

16. The process according to claim 15 for the oligomerisation of propene and/or $C_4$ olefins in which the temperature is in the range from 190° to 250° C.

17. The process according to claim 14 in which the solid phosphoric acid catalyst is hydrated by incorporating water in the feed.

18. The process according to claim 17 in which the water content of the feed is at least 0.06 mol %, based on the hydrocarbon content of the feed.

19. The process according to claim 18 in which the feed is subject to an alkaline wash to remove acidic polar species, followed by a weakly acidic water wash to produce a feed which is saturated with water at the temperature at which the water wash is performed.

20. The process according to claim 1 wherein the fluid material contained within the reactor tube is maintained substantially in a single liquid or dense phase.

21. The process according to claim 1 wherein the catalyst is disposed in a plurality of reactors in series.

22. The process according to claim 1 wherein the feed is distributed over a plurality of reactors in parallel.

23. The process according to claim 1 wherein the feed comprises propylene, wherein from 5 to 12 wt % of the olefins in the feed are pentenes, wherein up to 70 wt % of the feed comprises butene, in which the peak temperature is measured by means of a multipoint thermocouple disposed in the reactor tube, wherein control of the temperature control fluid parameters is accomplished by adjusting the temperature and/or the flow of said transfer fluid to maintain the peak temperature in the desired range, and wherein the peak temperature is maintained below 250° C.

* * * * *

UNITED STATES PATENT AND TRADEMARK OFFICE
CERTIFICATE OF CORRECTION

PATENT NO.       : 8,598,396 B2
APPLICATION NO. : 11/912762
DATED            : December 3, 2013
INVENTOR(S)      : Beadle et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1139 days.

Signed and Sealed this

Twenty-second Day of September, 2015

Michelle K. Lee
*Director of the United States Patent and Trademark Office*